(12) United States Patent
Masri et al.

(10) Patent No.: US 12,210,026 B2
(45) Date of Patent: Jan. 28, 2025

(54) ROBOTIC MODULAR GEOLOGIC CORE PREPARATION AND EXAMINATION TABLE

(71) Applicant: SAUDI ARABIAN OIL COMPANY, Dhahran (SA)

(72) Inventors: Abdul Hafiz O. Masri, Dhahran (SA); Mokhles M. Mezghani, Dhahran (SA); Mustafa A. Al Ibrahim, Safwa (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 259 days.

(21) Appl. No.: 17/817,243

(22) Filed: Aug. 3, 2022

(65) Prior Publication Data

US 2023/0073189 A1 Mar. 9, 2023

Related U.S. Application Data

(60) Provisional application No. 63/241,243, filed on Sep. 7, 2021.

(51) Int. Cl.
*G01N 33/24* (2006.01)
*G01N 35/00* (2006.01)

(52) U.S. Cl.
CPC ....... *G01N 35/00584* (2013.01); *G01N 33/24* (2013.01)

(58) Field of Classification Search
CPC .......................... G01N 35/00584; G01N 33/24
See application file for complete search history.

(56) References Cited

U.S. PATENT DOCUMENTS

| | | | | |
|---|---|---|---|---|
| 3,034,843 A | * | 5/1962 | Moon | F25D 15/00 312/277 |
| 3,217,672 A | | 11/1965 | Haughey | |
| 3,652,103 A | | 3/1972 | Higgs | |
| 3,786,932 A | | 1/1974 | Smith | |
| 4,590,866 A | * | 5/1986 | Schairbaum | A47B 17/02 434/323 |
| 5,499,697 A | | 3/1996 | Trimble et al. | |

(Continued)

FOREIGN PATENT DOCUMENTS

| CN | 202525486 U | * | 11/2012 |
|---|---|---|---|
| CN | 109380874 A | * | 2/2019 |

(Continued)

*Primary Examiner* — Jamel E Williams
(74) *Attorney, Agent, or Firm* — Osha Bergman Watanabe & Burton LLP (57) ABSTRACT

A modular geologic core examination table is claimed. The modular geologic core examination table includes at least two legs, each leg comprising an extending portion for increasing the effective length of each leg, the extending portion at least partially concentrically disposed within or around the leg from which it extends, and wheels affixed to each of the at least two legs, wherein the wheels comprise braking functionality. The modular geologic core examination table also includes a tabletop coupled to the at least two legs, the tabletop including a top surface for receiving a core sample tray configured to hold the geologic core samples, wherein the tabletop is disposed above an automated guided vehicle (AGV) configured to navigate the modular core examination table while carrying geologic core samples from one geologic processing station to another without collisions.

19 Claims, 4 Drawing Sheets

(56) References Cited

U.S. PATENT DOCUMENTS

| | | |
|---|---|---|
| 6,237,725 B1 | 5/2001 | Otterson et al. |
| 7,270,062 B1 * | 9/2007 | Larson .................... A47B 9/10 |
| | | 108/150 |
| 7,395,902 B2 | 7/2008 | D'Arca et al. |
| 8,490,555 B1 | 7/2013 | Agee |
| 9,826,825 B1 | 11/2017 | Jones et al. |
| 2002/0084389 A1 * | 7/2002 | Larson .................. A47B 21/00 |
| | | 248/371 |
| 2004/0135045 A1 * | 7/2004 | Larson ................ A47B 13/003 |
| | | 248/188.1 |
| 2005/0023787 A1 | 2/2005 | Haynes |
| 2021/0231631 A1 * | 7/2021 | Masri .................... A47B 37/00 |

FOREIGN PATENT DOCUMENTS

| | | | |
|---|---|---|---|
| CN | 214055513 U | * | 8/2021 |
| CN | 217861145 U | * | 11/2022 |
| WO | 2002024028 A1 | | 3/2002 |

\* cited by examiner

ROBOTIC MODULAR GEOLOGIC CORE PREPARATION AND EXAMINATION TABLE

BACKGROUND

Geologic cores, long cylindrical rock samples obtained from the subsurface formation, are essential data source in geoscientific studies. Such cores are commonly slabbed into two pieces along the length of the core and examined/ studied to determine characteristics and properties of the subsurface formation. Core samples may commonly undergo several activities which raise two main concerns minimizing the damage to the core samples (which often results in attempts to minimize handling), as well as improving the safety of the technicians and material handlers handling the core samples. Core samples are studied by geoscientists. The geologic core preparation and examination table therefore is required to be flexible and safe to use in multiple scenarios: 1) geologic core preparation involving initial core alignment and labeling process, 2) core loading and unloading, and 3) core examination. These scenarios require different setups and configurations of the table.

Core sample trays may be designed to accommodate a total weight of 75 kg (165 lbs.). Repeated-use type injuries to the back, neck, arms and other body parts may result from the strains of continually moving core samples and slabs from one table to the next. In addition, accident-type injuries may result from core samples falling from tables or off trays, which may increasingly result from cores and slabs being transferred from one inspection area to another, or to one or more storage areas. Geoscientists inspecting and studying the cores often find the viewing areas unsuitable (too high, too low, etc.) In addition, space for housing or storing needed equipment may be limited in the core sample viewing area.

Accordingly, there exists a need for a modular, automated table set up for geological cores.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a modular geologic core examination table. The modular geologic core examination table may include at least two legs, each leg comprising an extending portion for increasing the effective length of each leg, the extending portion at least partially concentrically disposed within or around the leg from which it extends, and wheels affixed to each of the at least two legs, wherein the wheels comprise braking functionality. The modular geologic core examination table may also include a tabletop coupled to the at least two legs, the tabletop including a top surface for receiving a core sample tray configured to hold the geologic core samples, wherein the tabletop is disposed above an automated guided vehicle (AGV) configured to navigate the modular core examination table while carrying geologic core samples from one geologic processing station to another without collisions.

In another aspect, embodiments disclosed herein relate to a geological core examination system. The geological core examination system may include a modular geological core examination table, configured to raise, lower, and tilt based, at least in part, on a user input; and an automated guided vehicle (AGV) fitted to the modular geological core examination table, wherein the AGV is configured to navigate the modular geologic core examination table while carrying geologic core samples from one geologic processing station to another without collisions.

DETAILED DESCRIPTION

Figure 2:
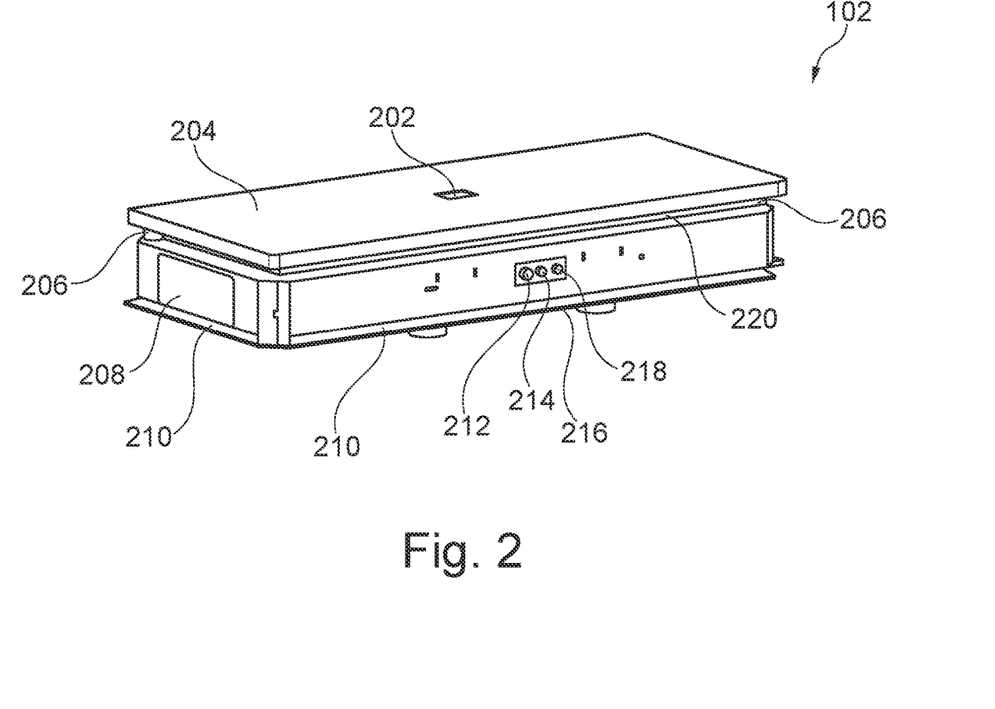
FIG. 2 shows an example automated guided vehicle (AGV) component of the robotic modular geologic core examination table in accordance with one or more embodiments.
Figure 3:
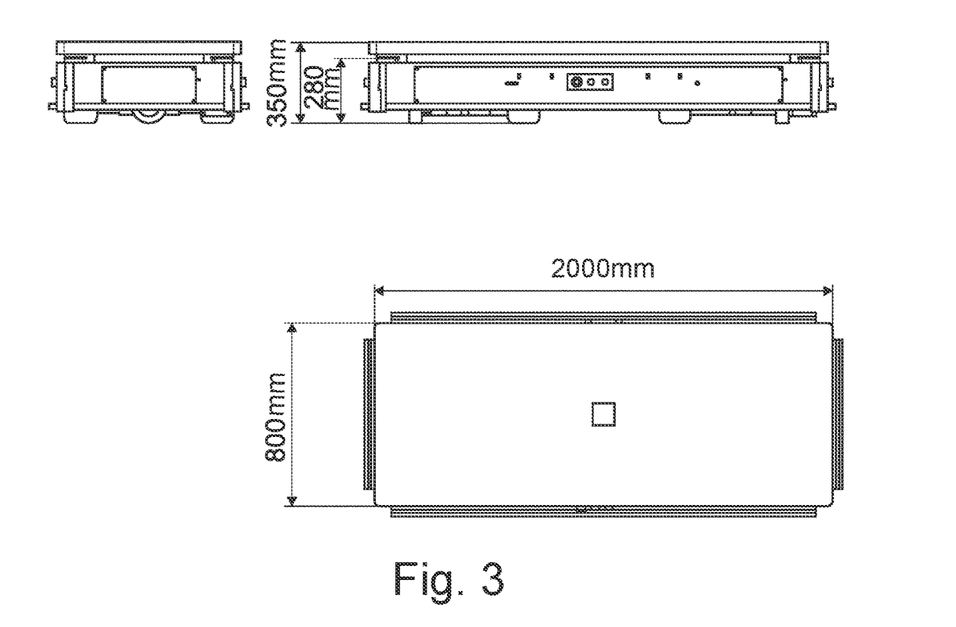
FIG. 3 shows example dimensions of the robotic modular geologic core examination table shown in FIG. 1 in accordance with one or more embodiments.

In one aspect, embodiments disclosed herein relate to a robotic geologic core examination table that is modular to handle all of geologic core preparation involving initial core alignment and labeling process, core loading and unloading, and core examination. Three design principles are used when designing the table: 1) safety, 2) mobility, and 3) versatility. The table is heavy and should move in a predesigned workflow. Embodiments disclosed herein relate to an automated, mobile geologic core examination table that moves from one processing station to another efficiently and safely. The design of the robotic modular geologic core examination table is described herein in two parts: 1) the table design (FIG. 1); and 2) the automated guided vehicle (AGV) design (FIGS. 2-3).

Figure 1:
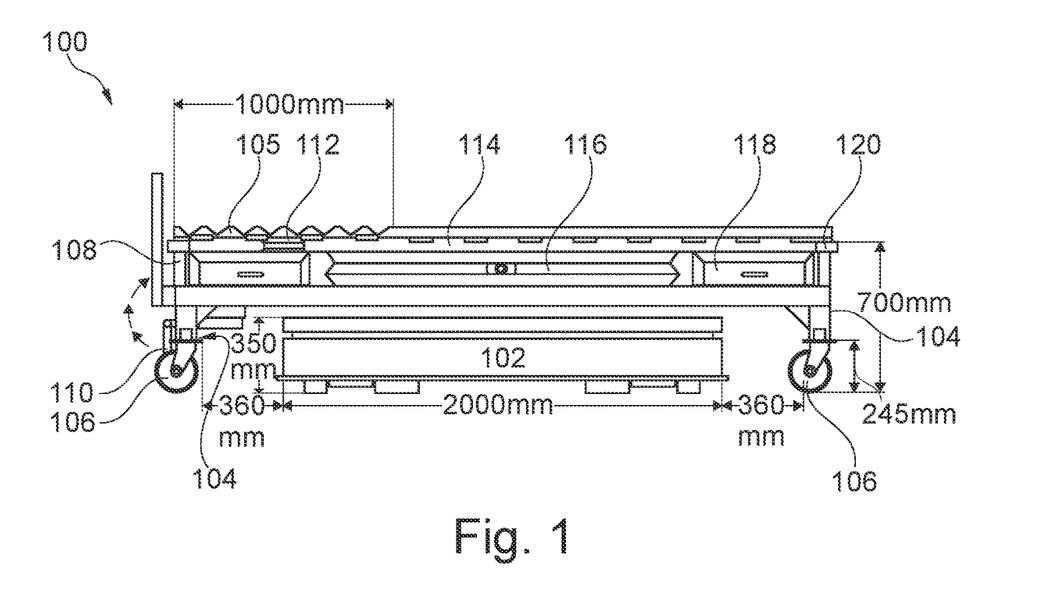
FIG. 1 shows a robotic modular geologic core examination table in accordance with one or more embodiments.

FIG. 1 shows the geologic core examination table (100) (also called inspection table herein) features with the robotic AGV (102) aspect for lifting and tilting the table. In particular, FIG. 1 shows a side view of the geologic core examination table (100) which has at least two legs (104) and is mobile with wheels (106). The wheels are heavy duty wheels with automatic braking functionality for safety purposes. Different systems known to those of ordinary skill in the art may be used for implementing the brakes. The wheels shown in FIG. 1 are 400 kg capacity swivel wheel with a dead man's brake. In one or more embodiments, the braking system may be implemented in any number of wheels, i.e., a single wheel, 2 wheels, or all four wheels, for example. The automatic braking system is capable of being disengaged by adjusting a locking mechanism. This is important to have when connecting two or more tables together as described below.

In some embodiments, the geologic core inspection table includes at least four legs. At least two legs include a bottom portion extending parallel to the ground. In some embodiments, at least two legs comprising an upside-down "T" shape or an "I" shape.

Figure 5A:
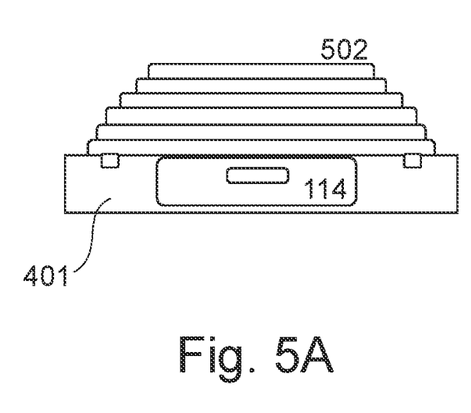
FIGS. 5A and 5B show a top portion of the robotic modular geologic core examination table in accordance with one or more embodiments.

A tabletop is disposed above and coupled to the legs (104), the tabletop including a surface for receiving the core tray (105). In one or more embodiments, the tabletop of the geologic core examination table is made of cylindrical rollers, as shown in FIG. 5A below. In some embodiments, the tabletop includes a retractable movable core tray (105) coupled to a bottom surface of the tabletop. The core tray (105) is for holding core samples, and may include two or more grooves disposed therein, each groove of the two or more grooves extending longitudinally for receiving a core sample.

When the table needs to be moved, a handle (110) is pressed or pushed with a foot (a foot pump) while pushing the cart, in the direction indicated by the arrows in FIG. 1. In one or more embodiments, as shown in FIG. 1, the handle (110) is disposed under the tabletop on the width side. In other example embodiments, the handle (110) is on the side of the table but may be moved to under the table when it is not in use. This is important to allow multiple tables to be stacked. The inspection table may also include one or more automatic braking disengagement handles (or levers) that may be used to temporarily or permanently disengage the brake from the wheel (106). In one embodiment, multiple inspection tables may be coupled together (for example, via one or more rigid attachments disposed underneath tabletop) such that the multiple inspection tables may be moved simultaneously by a single operator. When multiple inspection tables are coupled, the automatic braking disengagement handle may be used to disengage the brake on one table, allowing the operator to use the brake release of the other table as a braking mechanism for both tables, thereby requiring the operator to squeeze only a single brake release in order to move or maneuver multiple inspection tables simultaneously.

In one or more embodiments, the geologic core examination table (100) length and width is configured to handle the same number of trays. For example, a table width of 100 cm and length of 300 cm would correspond to a V-type core tray (105) width of 25 cm, and length of 100 cm. In the example scenario with the dimensions above, the result would be a geologic core examination table that can accommodate 12 trays that can be arranged in both directions, with enough head under the table to have the AGV lifting the table to move it.

Continuing with FIG. 1, a retractable tray with raised edges is available on each elongate side of the geologic core examination table. The tray may be used to hold working material of the geoscientist such as papers, pens, hand lens, acid bottles, grain size charts, rulers, and laptops. A clear, acrylic label holder (112) is also shown that can store labels that scientists may need to label the geologic cores being examined on the tabletop. An elongate groove in the tray is specifically designed to hold two pens from rolling. The trays can also be moved along the table to accommodate the user examining the geologic core(s) slabs as the user describes the core. In one or more embodiments, the tray is configured to move along the length of the table using any suitable means, such as a wheel attached to the underside of the geologic core examination table. The tray may be completely pushed under the table when it is not needed and may be pulled out/retracted using a hinge that locks the tray into place.

The table is customized with features specifically designed to accommodate the needed safety, mobility, and versatility of usage. The table is capable of adjusting height and tilt, accommodating different core tray configurations, automated moving, and storing needed equipment. In one or more embodiments, a plate with screws may be used to attach the extending portion of each leg (104) to the tabletop. In other embodiments, each leg may pivot on the respective wheel (106) at an interface between the leg (104) and the wheel (106), such that the linkages or couplings between the legs (104) and the tabletop may be fixed even if one side of the inspection table is being raised higher than the other. The user or operator may control all four corners (that is, all four legs (104)) at the same time via the control console, raising and lowering all four legs while the tabletop remains parallel to the ground. In another implementation of the present embodiments, the user or operator may control two corners (along the same length of the inspection table as each other) in order to tilt the inspection table for ease of viewing. Raising or tilting of the inspection table may be done while the geologic cores are on the tabletop, thus, mechanisms discussed below prevent the cores from falling, slipping, or otherwise being damaged during movement.

Core trays are designed specifically to handle slabbed geologic core. Chaining of tables is possible when extra space is needed. Because the geologic core examination table is used in semi-industrial zone and need to handle heavy loads, e.g., minimum of 500 kg and up to 750 kg, and the geologic core examination table needs to be portable, it needs to be light. In one or more embodiments, the material of the geologic core examination table is industrial grade galvanized stainless steel. However, those skilled in the art will appreciate that the table may be made of other materials, such as austenitic steel, carbon steel, titanium, or a combination thereof.

In one or more embodiments, a hydraulic system is used to adjust the height as described above. The hydraulic system includes a pneumatic cylinder disposed at least partially within a hollow interior of a leg, hydraulic fluid disposed within the pneumatic cylinder, and a hydraulic fluid pressure source fluidly connected to the hydraulic fluid. The hydraulic system may include at least one extending portion of the table leg (104) for extending (or retracting) each table leg (104), thereby raising or lowering the height of the tabletop. In one or more embodiments, the at least one extending portion may be a telescopic slider (108). The hydraulic system may also include hydraulic fluid (not shown) disposed within the hollow interior of one or more table legs (104), the hollow interior acting as a pneumatic cylinder. The hydraulic system may also include one or more pumps or compressors (116) for pressurizing the hydraulic fluid. In addition, one or more control consoles (shown in FIGS. 4A and 4B below) may be operatively coupled to the hydraulic system such that an operator may press an up button or down button as needed to raise and lower the tabletop.

Further, all edges of the geologic core examination table may be blunted to prevent injury. In addition, rubber bumpers or stoppers (120) on the table corners may be used to increase safety. The table may be coated or painted for aesthetic purposes. Further, moveable side stopper (114) prevents core sample trays from sliding or falling. In one or more embodiments, the side stopper (114) may be pulled vertically upward from the side of the tabletop to provide a barrier preventing the core tray (105) and core sample from sliding off the inspection table. The side stopper (114) may include one or more handles disposed within it, thereby allowing an operator to easily slide the side stopper up and down (seen in FIGS. 4A and 4B).

In one or more embodiments, the tabletop may include two drawers (118) that may be used store tools for inspecting the geologic cores. Two electrical outlets (not shown) may be included/available in each elongate side of the table. These can be used to power different devices such as laptops or small microscopes. A switch for the electrical outlets is available in the console (see (406) in FIGS. 4A and 4B). In addition, an electrical outlet may be included/available in the retractable tray for usage with equipment on the tray.

The height of the table (100) from the wheel to the tabletop is a minimum of 700 mm, as labeled in FIG. 1. Dimensions of other components, such as the AGV (102) shown in FIG. 1, are explained further in FIG. 3 described below.

FIG. 2 shows an expanded view and the robotic components of the AGV (102) of FIG. 1 accordance with one or more embodiments. That is, FIG. 2 shows the AGV (robotic) part on top of which the geologic core examination tabletop and core tray sit. The AGV (102) shown in FIG. 2 is the functionality that imparts robotic operation to the table and is configured to move the table from one core processing station to another autonomously. In one or more embodiments, the table may be disposed on the AGV robot. For example, the table may be mounted on top of the AGV. AGV is a portable robot that follows along marked long lines or wires on the floor, or uses radio waves, vision cameras, magnets, or lasers for navigation. AGV technology is often used in industrial applications to transport heavy materials around a large industrial building, such as a factory or warehouse. The AGV is configured to store objects on a bed. The objects can be placed on a set of motorized rollers (conveyor) and then pushed off by reversing them. In one or more embodiments, the AGV is designed to lift the table and move it from a designated station to another designated station with a defined workflow to perform the geological core preparation.

In one or more embodiments, the AGV (102) is configured with a top camera (202), a bottom camera (216), a front camera (208), a loading body lifting surface (204), a safety laser scanner/sensor from both sides (206), an anti-collision edge sensor (210), and several buttons (212, 214, 218) for starting/stopping the automatic movement of the geologic core examination table or of the AGV component of the table. Each of the aforementioned components of the AGV (102) facilitate navigation of the AGV using one or more of the following mechanisms.

Wired. In wired navigation, a slot is cut into the floor and a wire is placed approximately 1 inch below the surface. This slot is cut along the path the AGV is to follow. This wire is used to transmit a radio signal. A sensor is installed on the bottom of the AGV close to the ground. The sensor detects the relative position of the radio signal being transmitted from the wire. This information is used to regulate the steering circuit, making the AGV follow the wire.

Guide tape. AGV (102) may use tape for the guide path. The tapes can be one of two styles: magnetic or colored. The AGV is fitted with the appropriate guide sensor to follow the path of the tape. One major advantage of tape over wired guidance is that it can be easily removed and relocated if the course needs to change. Colored tape is initially less expensive but lacks the advantage of being embedded in high traffic areas where the tape may become damaged or dirty. A flexible magnetic bar can also be embedded in the floor like wire but works under the same provision as magnetic tape and so remains unpowered or passive. Another advantage of magnetic guide tape is the dual polarity. Small pieces of magnetic tape may be placed to change states of the AGC based on polarity and sequence of the tags.

Laser target navigation. The navigation is done by mounting reflective tape on walls, poles or fixed machines. The AGV carries a laser transmitter and receiver on a rotating turret. The laser is transmitted and received by the same sensor. The angle and (sometimes) distance to any reflectors that in line of sight and in range are automatically calculated. This information is compared to the map of the reflector layout stored in the AGV's memory. This allows the navigation system to triangulate the current position of the AGV. The current position is compared to the path programmed in to the reflector layout map. The steering is adjusted accordingly to keep the AGV on track. It can then navigate to a desired target using the constantly updating position. The use of modulated laser light gives greater range and accuracy over pulsed laser systems. By emitting a continuous fan of modulated laser light a system can obtain an uninterrupted reflection as soon as the scanner achieves line of sight with a reflector. The reflection ceases at the trailing edge of the reflector which ensures an accurate and consistent measurement from every reflector on every scan. By using a modulated laser a system can achieve an angular resolution of ~0.1 mrad (0.006°) at 8 scanner revolutions per second. A pulsed laser scanner emits pulsed laser light at a rate of 14,400 Hz which gives a maximum possible resolution of 3.5 mrad (0.2°) at 8 scanner revolutions per second. To achieve a workable navigation, the readings must be interpolated based on the intensity of the reflected laser light, to identify the centre of the reflector.

The safety laser scanner/sensor (206) on either side of the AVG (102) may be used with laser target navigation of the AGV (102) or may be provided as an additional safety mechanism to be used with all of the other navigation mechanisms discussed herein. The laser scanner/sensor (206) may employ HDDM scanning technology, and is highly resistant to dirt, dust, and ambient light to deliver high-precision measurement data. The safety laser scanner/sensor may be integrated with a variety of control systems. The anti-collision edge sensor (210) is another safety sensor that senses/measures the AGV's position and movement and prevents collision with another object. The sensor reacts to direct obstruction when the geologic core examination table's height is adjusted either up or down, or when the geologic core examination table is moving using the AGV technology. LiDAR scanners, sometimes referred to as line-scanners may also be used to implement the anti-collision edge sensor. These use monochromatic laser light, sent through a fiber optic system or a scanning mirror and emitted in a two-dimensional plane transverse to the direction of motion.

Inertial (Gyroscopic) Navigation. Another form of an AGV guidance is inertial navigation. With inertial guidance, a computer control system directs and assigns tasks to the vehicles. Transponders are embedded in the floor of the workplace. The AGV uses these transponders to verify that the vehicle is on course. A gyroscope is able to detect the slightest change in the direction of the vehicle and corrects it in order to keep the AGV on its path. The margin of error for the inertial method is ±1 inch. Inertial can operate in nearly any environment including tight aisles or extreme temperatures. Inertial navigation can include use of magnets embedded in the floor of the facility that the vehicle can read and follow.

Natural feature (Natural Targeting). Navigation without retrofitting of the workspace is called Natural Features or Natural Targeting Navigation. One method uses one or more range-finding sensors, such as a laser range-finder, as well as gyroscopes or inertial measurement units with Monte-Carlo/Markov localization techniques to understand where it is as it dynamically plans the shortest permitted path to its goal. The advantage of such systems is that they are highly flexible for on-demand delivery to any location. They can handle failure without bringing down the entire manufacturing operation, since AGVs can plan paths around the failed device. They also are quick to install, with less down-time for the factory.

Vision-Guidance. Vision-Guided AGVs can be installed with no modifications to the environment or infrastructure. They operate by using cameras to record features along the route, allowing the AGV to replay the route by using the recorded features to navigate. Vision-Guided AGVs use Evidence Grid technology, an application of probabilistic volumetric sensing, and was invented and initially developed by Dr. Hans Moravec at Carnegie Mellon University. The Evidence Grid technology uses probabilities of occupancy for each point in space to compensate for the uncertainty in the performance of sensors and in the environment. The primary navigation sensors are specially designed stereo cameras. The vision-guided AGV uses 360-degree images and build a 3D map, which allows the vision-guided AGVs to follow a trained route without human assistance or the addition of special features, landmarks or positioning systems. Thus, with this mechanism of navigation, the cameras (202, 208, 216) are configured to provide a surrounding view of the AVG robot so that the AGV robot can "see" where to move to get from one station to another while avoiding collisions. The cameras (202, 208, 216) may be any suitable type of video camera capable of real-time video of the surroundings of the AVG robot, a smart device such as a phone or tablet, or any other camera device. Each of the top, bottom, and front cameras may be the same type of camera or different types of cameras.

Geoguidance. A geoguided AGV recognizes its environment to establish its location. Without any infrastructure, the forklift equipped with geoguidance technology detects and identifies columns, racks and walls within the warehouse. Using these fixed references, it can position itself, in real time and determine its route. There are no limitations on distances to cover number of pick-up or drop-off locations. Routes are infinitely modifiable.

Each of the emergency stop, the start and stop buttons (212, 214, 218) may be any type of suitable button such as a push button, lever, toggle switches, E-stop buttons, etc., designed to start AVG navigation, stop AVG navigation, or completely shut off the AGV in an emergency.

In one or more embodiments, the AGV is configured to lift the tabletop on which geologic cores sit and where they are examined. The loading body lifting device (204) of the AGV is configured to lift and tilt the tabletop for examination of the geologic cores on the tabletop. The loading body lifting device (204) may be any suitable lifting mechanism, such as a mechanical lifting structure. For example, the loading body lifting device (204) and may employ pneumatic/electronic/hydraulic linear actuators, air bellows, electromagnets, shafts, etc.

The AGV (102) may be protected from dirt, dents, etc., by a seal protection (220) on the top surface, where the top camera and protective panel (202) are located.

Those skilled in the art will appreciate that although not shown, the AGV may include one or more processors to process sensor and camera data and memory to store navigation related data such as pathways previous traveled, etc. In one or more embodiments, the AGV may also include artificial intelligence capability in the form of machine learning algorithms that are trained based on previous navigation of the AGV from processing station to processing station. Any suitable machine learning algorithms may be employed to train the AGV to recognize, remember, and learn from navigation paths.

FIG. 3 illustrates the robotic modular geologic core examination table dimensions. In one or more embodiments, the geologic core examination table dimensions are approximately 2000 mm long, 800 mm wide and 350 mm high with a lifting margin of 100 mm. Those skilled in the art will appreciate that the dimensions shown in FIG. 3 are merely provided by way of an example of the length, width, and height of a AGV as disclosed herein. The dimensions may be any suitable dimensions for carrying, displaying, and moving geologic cores on a tabletop that is disposed on top of the AGV without departing from the scope herein.

Figure 4A:
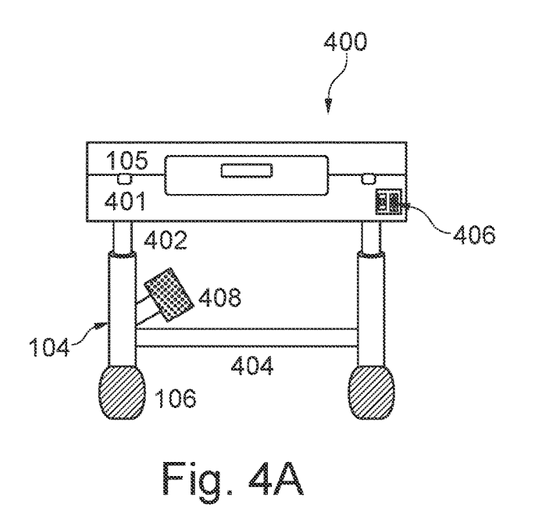
FIGS. 4A and 4B show different views and positions of the robotic modular geologic core examination table in accordance with one or more embodiments.
Figure 4B:
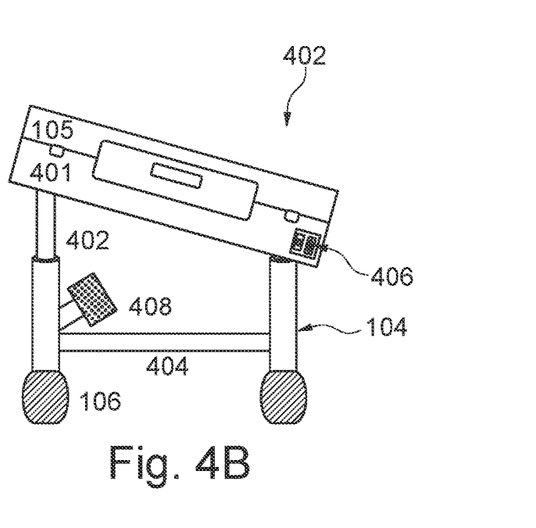

In the embodiment of FIGS. 4A and 4B, the geologic core examination table includes a tabletop (401), a core tray (105) on top of the tabletop (401), a hydraulic system (402) and a shelf (404). FIG. 4A shows a width view of the upright position (400), and FIG. 4B shows a tilted position (402) of the tabletop (401). Each of the tabletop (401) and the shelf (404) must be sturdy enough to accommodate several hundred kilograms. The height of the table is adjustable by a user. In one or more embodiments, a hydraulic system (402) is used to adjust the height as described above. Further, in one or more embodiments, the hydraulic system (402) may include a telescopic slider (108). In the embodiment of FIGS. 4A and 4B, the inspection table includes a hydraulic system (402) only on the left leg (104). In other embodiments, each leg (104) may include a separate hydraulic system (402), or interconnected components of a single hydraulic system. For example, in one or more embodiments, the tabletop (401), the shelf (404), or both the tabletop (401) and the shelf (404) may include one or more fluid passageways to fluidly connect the pneumatic cylinders within multiple legs (104) of the inspection table. In other embodiments, the hydraulic system (402) may be adjusted using a console (406) mounted on one end of the table, or a manual lever (408) or wheel to be used in case of power outages or console failure. Those skilled in the art will appreciate that the tabletop (401) may be raised or tilted using other means without departing from the scope herein. For example, an electric motor (which may include one or more gears, linkages, or other actuators) may be used to raise and lower the tabletop (401), rather than a hydraulic system.

In one implementation, the user can only control all four corners at the same time. In another implementation, the user can control two corners (connected at table length) at a time to tilt the table for ease of viewing as shown in FIGS. 4A and 4B. The movable sides and the tray interlocking system are used to prevent the core tray from falling. As noted above, the system can be controlled electrically using the console (406) or manually.

Figure 5B:
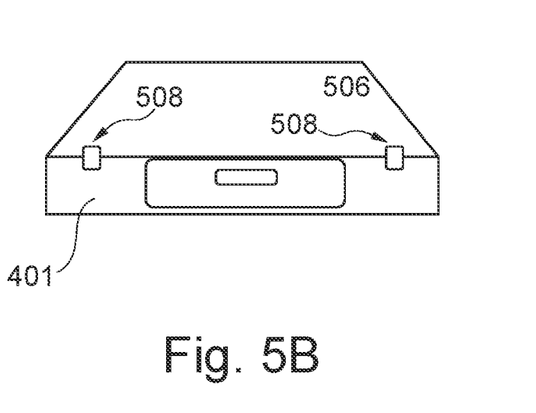

In one or more embodiments, the tabletop (401) of the geologic core examination table is made of cylindrical rollers, as shown in FIG. 5A. FIG. 5A illustrates, a perspective side view of the tabletop, according to aspects of the present disclosed embodiments. In the embodiment of FIG. 5, the tabletop (401) includes the side stopper (114) and a plurality of rollers (502), which may be used to slide heavy core trays across the top of the tabletop (401) without the operator, geoscientist, material handler, or technician needing to lift the core trays. For example, the rollers (502) may be cylindrically shaped and may have a diameter from about three (3) cm to about five (5) cm, or from about 3.6 cm to about 4.0 cm. A gap of from about one (1) cm to about five (5) cm, or from about two (2) cm to about four (4) cm may be disposed between each roller (502). The rollers (502) allow the core trays (502) to be easily pushed into place during loading and unloading procedures. The rollers can be covered, if needed, as shown in FIG. 5B, with a detachable sheet cover (506) that can lock into the table using one or more locks (508). Locks (508) keep the cover in place. The locks (508) may include a clip that engages one or more lips, holes, tabs, tangs, grooves, or other potential locking features of each of the core trays and tabletop. In another embodiment, one end of each lock may be permanently fixed to the tabletop (401).

The cover (506) may be composed of a flexible material (or may include a flexible or malleable sheet) that is wound (and subsequently unwound from) a scroll disposed at one of the width ends of the inspection table. The cover (506) may be manually pulled across the rollers (502) and latched or locked into place via one or more side locks (508) disposed at one of the width ends of the inspection table. In other embodiments, the cover may be wound and unwound using a turning motor (not shown) coupled to the scroll. In still other embodiments, the cover (506) may be more rigid and may be placed manually over the rollers (502) such that the rigid cover (506), in connection with the rollers (502) are able to support the weight of the loaded core samples trays. One or more runners, guides, or grooves in the tabletop (not shown) along each side length of the inspection table may be used to ensure that the cover (506) remains aligned above the rollers (502). The cover (506) may be used to restrict the movement of the core trays on top of the tabletop (401) such that they do not slide across the surface as easily. In one embodiment, the cover (506) may include a plurality of interlocked smaller sheets. In another implementation, a more malleable sheet or a sheet composed of interlocked smaller sheets is rolled under the table using an electric motor or manually, similar to a car garage. The sheet is guided into place automatically through a designed groove in the tabletop. This implementation prevents the need to store the sheet externally when not in use and makes the installation easier.

Figure 6:
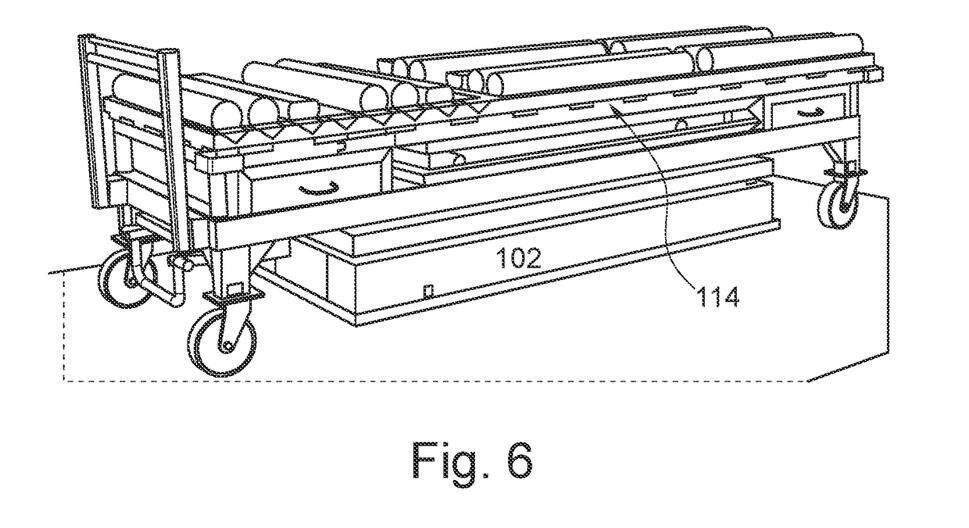
FIG. 6 shows an angled side view of the robotic modular geologic core examination table with a fixed side stopper in accordance with one or more embodiments.

In each of the embodiments of FIGS. 5A and 5B, the side stopper (114) is in a retracted position. As shown more clearly in FIG. 6, an angled side view of the table (100) is shown, with the rollers clearly shown and a fixed side stopper (114) is used to secure the trays in place and prevent accidents.

In one or more embodiments, two or more tables may be attached to each other through a rigid attachment from the underside of the tabletop (401). If this is done, the braking system is disengaged in one of the tables in order to move the assembly.

Figure 7:
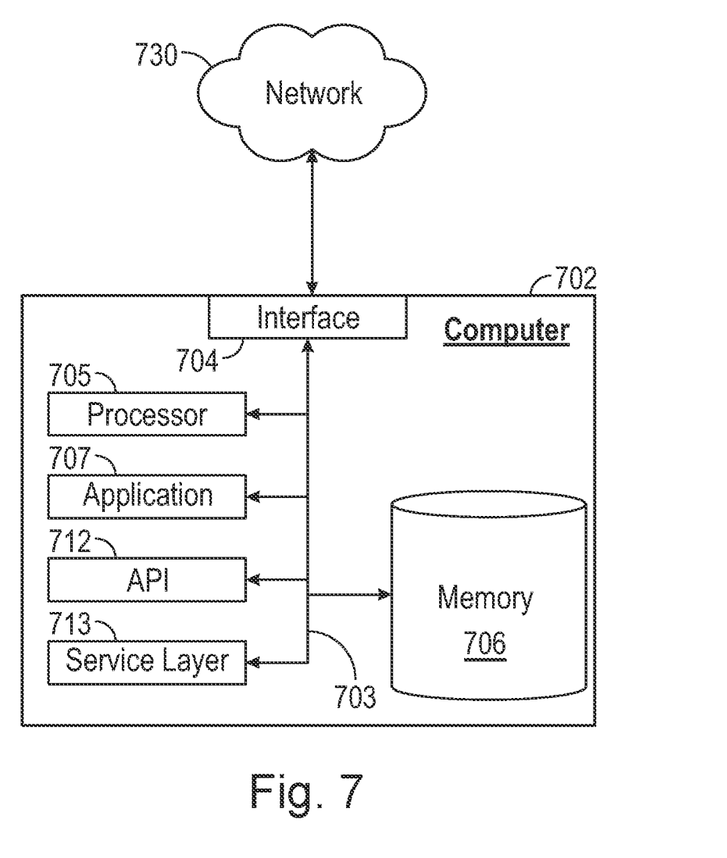
FIG. 7 shows a computer system in accordance with one or more embodiments.

FIG. 7 depicts a block diagram of a computer system (702) used to provide computational functionalities associated with described algorithms, methods, functions, processes, flows, and procedures as described in this disclosure, according to one or more embodiments. More specifically, FIG. 7 depicts a block diagram of a computer system (702) which may be implemented, for example, in the console (406) or in the AGV (102). The illustrated computer (702) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (702) may include a computer that includes an input device, such as a keypad, keyboard, touch screen, or other device that can accept user information, and an output device that conveys information associated with the operation of the computer (702), including digital data, visual, or audio information (or a combination of information), or a GUI.

The computer (702) can serve in a role as a client, network component, a server, a database or other persistency, or any other component (or a combination of roles) of a computer system for performing the subject matter described in the instant disclosure. The illustrated computer (702) is communicably coupled with a network (730). In some implementations, one or more components of the computer (702) may be configured to operate within environments, including cloud-computing-based, local, global, or other environment (or a combination of environments).

At a high level, the computer (702) is an electronic computing device operable to receive, transmit, process, store, or manage data and information associated with the described subject matter. According to some implementations, the computer (702) may also include or be communicably coupled with an application server, e-mail server, web server, caching server, streaming data server, business intelligence (BI) server, or other server (or a combination of servers).

The computer (702) can receive requests over network (730) from a client application (for example, executing on another computer (702)) and responding to the received requests by processing the said requests in an appropriate software application. In addition, requests may also be sent to the computer (702) from internal users (for example, from a command console or by other appropriate access method), external or third-parties, other automated applications, as well as any other appropriate entities, individuals, systems, or computers.

Each of the components of the computer (702) can communicate using a system bus (703). In some implementations, any or all of the components of the computer (702), both hardware or software (or a combination of hardware and software), may interface with each other or the interface (704) (or a combination of both) over the system bus (703) using an application programming interface (API) (712) or a service layer (713) (or a combination of the API (712) and service layer (713). The API (712) may include specifications for routines, data structures, and object classes. The API (712) may be either computer-language independent or dependent and refer to a complete interface, a single function, or even a set of APIs. The service layer (713) provides software services to the computer (702) or other components (whether or not illustrated) that are communicably coupled to the computer (702). The functionality of the computer (702) may be accessible for all service consumers using this service layer. Software services, such as those provided by the service layer (713), provide reusable, defined business functionalities through a defined interface. For example, the interface may be software written in JAVA, C++, or other suitable language providing data in extensible markup language (XML) format or another suitable format. While illustrated as an integrated component of the computer (702), alternative implementations may illustrate the API (712) or the service layer (713) as stand-alone components in relation to other components of the computer (702) or other components (whether or not illustrated) that are communicably coupled to the computer (702). Moreover, any or all parts of the API (712) or the service layer (713) may be implemented as child or sub-modules of another software module, enterprise application, or hardware module without departing from the scope of this disclosure.

The computer (702) includes an interface (704). Although illustrated as a single interface (704) in FIG. 7, two or more interfaces (704) may be used according to particular needs, desires, or particular implementations of the computer (702). The interface (704) is used by the computer (702) for communicating with other systems in a distributed environment that are connected to the network (730). Generally, the interface (704) includes logic encoded in software or hardware (or a combination of software and hardware) and operable to communicate with the network (730). More specifically, the interface (704) may include software supporting one or more communication protocols associated with communications such that the network (730) or interface's hardware is operable to communicate physical signals within and outside of the illustrated computer (702).

The computer (702) includes at least one computer processor (705). Although illustrated as a single computer processor (705) in FIG. 7, two or more processors may be used according to particular needs, desires, or particular implementations of the computer (702). Generally, the computer processor (705) executes instructions and manipulates data to perform the operations of the computer (702) and any machine learning networks, algorithms, methods, functions, processes, flows, and procedures as described in the instant disclosure.

The computer (702) also includes a memory (706) that holds data for the computer (702) or other components (or a combination of both) that can be connected to the network (730). For example, memory (706) can be a database storing data consistent with this disclosure. Although illustrated as a single memory (706) in FIG. 7, two or more memories may be used according to particular needs, desires, or particular implementations of the computer (702) and the described functionality. While memory (706) is illustrated as an integral component of the computer (702), in alternative implementations, memory (706) can be external to the computer (702).

The application (707) is an algorithmic software engine providing functionality according to particular needs, desires, or particular implementations of the computer (702), particularly with respect to functionality described in this disclosure. For example, application (707) can serve as one or more components, modules, applications, etc. Further, although illustrated as a single application (707), the application (707) may be implemented as multiple applications (707) on the computer (702). In addition, although illustrated as integral to the computer (702), in alternative implementations, the application (707) can be external to the computer (702).

There may be any number of computers (702) associated with, or external to, a computer system containing a computer (702), wherein each computer (702) communicates over network (730). Further, the term "client," "user," and other appropriate terminology may be used interchangeably as appropriate without departing from the scope of this disclosure. Moreover, this disclosure contemplates that many users may use one computer (702), or that one user may use multiple computers (702).

Embodiments of the present disclosure may provide at least one of the following advantages. The table disclosed herein provides all the features needed for both core preparations and examinations in one package. The table has mobility using AGV and is height or tilt adjustable. The geologic core examination table comes with a specification to fit with the table and move it from one station to another with a predefined workflow. The geologic core examination table and tray are specifically designed to fit together perfectly. Furthermore, trays can be locked into place in the width side of the table. The tray design is unique with two trays for slabbed core and locks on the side to allow connecting multiple trays. The geologic core examination table disclosed herein can be chained to other similar tables or any custom apparatus. Rollers in the tables can be covered so that the tabletop can be converted into a flat tabletop.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A modular geologic core examination table, comprising:
   at least two legs, each leg comprising an extending portion for increasing the effective length of each leg, the extending portion at least partially concentrically disposed within or around the leg from which it extends;
   wheels affixed to each of the at least two legs, wherein the wheels comprise braking functionality; and
   a tabletop coupled to the at least two legs, the tabletop including a top surface for receiving a core sample tray configured to hold the geologic core samples,
   wherein the tabletop is disposed above an automated guided vehicle (AGV) configured to navigate the modular geologic core examination table while carrying geologic core samples from one geologic processing station to another without collisions, and
   wherein the tabletop comprises a plurality of cylindrical rollers.

2. The modular geologic core examination table of claim 1, further comprising a hydraulic system installed between at least one leg and the tabletop, wherein the hydraulic system comprises one or more pneumatic cylinders.

3. The module geologic core examination table of claim 2, wherein the hydraulic system comprises a telescopic slider.

4. The modular geologic core examination table of claim 2, further comprising one or more control consoles operatively coupled to the hydraulic system.

5. The modular geologic core examination table of claim 2, further comprising a manual lever coupled to the hydraulic system.

6. The modular geologic core examination table of claim 2, further comprising one or more fluid passageways fluidly connecting the hydraulic system to one or more legs.

7. The modular geologic core examination table of claim 1, further comprising a detachable sheet cover secured on top of the plurality of cylindrical rollers with one or more locks.

8. The modular geological core examination table of claim 1, further comprising a rigid attachment secured to an underside of the tabletop and a second modular geological core examination table attached to the modular geological core examination table at the rigid attachment.

9. The modular geological core examination table of claim 1, wherein braking functionality comprises a handle secured to the table, wherein the handle is movable to lock and unlock the wheels.

10. The modular geological core examination table of claim 1, further comprising a retractable tray configured to extend from beneath the tabletop, wherein the retractable tray has one or more integrally formed grooves and one or more raised edges.

11. The modular geological core examination table of claim 1, wherein the core sample tray has two or more grooves extending longitudinally across the core sample tray.

12. A geological core examination system, comprising:
a modular geological core examination table, configured to raise, lower, and tilt based, at least in part, on a user input; and
an automated guided vehicle (AGV) fitted to the modular geological core examination table, wherein the AGV is configured to navigate the modular geologic core examination table while carrying geologic core samples from one geologic processing station to another without collisions.

13. The geological core examination system of claim 12, wherein the modular geological core examination table comprises:
at least two legs, each leg comprising an extending portion for increasing the effective length of each leg, the extending portion at least partially concentrically disposed within or around the leg from which it extends;
wheels affixed to each of the at least two legs, wherein the wheels comprise braking functionality; and
a tabletop disposed above the AGV and coupled to the at least two legs, the tabletop including a top surface for receiving a core sample tray configured to hold the geologic core samples.

14. The geological core examination system of claim 13, further comprising a hydraulic system installed between at least one leg and the tabletop, wherein the hydraulic system comprises one or more pneumatic cylinders.

15. The geological core examination system of claim 14, wherein the user input is generated at one or more control consoles operatively coupled to the hydraulic system.

16. The geological core examination system of claim 14, further comprising one or more fluid passageways fluidly connecting the hydraulic system to one or more legs.

17. The geological core examination system of claim 13, further comprising a rigid attachment secured to an underside of the tabletop and a second modular geological core examination table attached to the modular geological core examination table at the rigid attachment.

18. The modular geological core examination table of claim 13, further comprising a retractable tray configured to extend from beneath the tabletop, wherein the retractable tray has one or more integrally formed grooves and one or more raised edges.

19. The modular geological core examination table of claim 13, wherein the core sample tray has two or more grooves extending longitudinally across the core sample tray.

* * * * *